United States Patent
Röder et al.

(10) Patent No.: US 10,713,590 B2
(45) Date of Patent: Jul. 14, 2020

(54) BAGGED FILTERING METHOD FOR SELECTION AND DESELECTION OF FEATURES FOR CLASSIFICATION

(71) Applicant: Biodesix, Inc., Boulder, CO (US)

(72) Inventors: Heinrich Röder, Steamboat Springs, CO (US); Joanna Röder, Steamboat Springs, CO (US); Arni Steingrimsson, Steamboat Springs, CO (US); Carlos Oliveira, Steamboat Springs, CO (US)

(73) Assignee: BIODESIX, INC., Boulder, CO (US)

( * ) Notice: Subject to any disclaimer, the term of this patent is extended or adjusted under 35 U.S.C. 154(b) by 1136 days.

(21) Appl. No.: 15/091,417

(22) Filed: Apr. 5, 2016

(65) Prior Publication Data

US 2016/0321561 A1   Nov. 3, 2016

Related U.S. Application Data

(60) Provisional application No. 62/154,844, filed on Apr. 30, 2015.

(51) Int. Cl.
*G06N 20/00* (2019.01)
*G16B 40/00* (2019.01)
*G16H 10/40* (2018.01)

(52) U.S. Cl.
CPC .......... *G06N 20/00* (2019.01); *G16B 40/00* (2019.02); *G16H 10/40* (2018.01)

(58) Field of Classification Search
CPC .......... G06N 20/00; G16B 40/00; G16H 10/40
See application file for complete search history.

(56) References Cited

U.S. PATENT DOCUMENTS

| 7,736,905 B2 | 6/2010 | Roder et al. |
| 9,279,798 B2 | 3/2016 | Roder et al. |

(Continued)

OTHER PUBLICATIONS

Sotiris Kotsiantis, "Combining bagging, boosting, rotation forest, and random subspace methods", Springer, Dec. 2010. (Year: 2010).*

(Continued)

*Primary Examiner* — Benjamin P Geib
(74) *Attorney, Agent, or Firm* — DLA Piper LLP

(57) ABSTRACT

Classifier generation methods are described in which features used in classification (e.g., mass spectral peaks) are selected, or deselected using bagged filtering. A development sample set is split into two subsets, one of which is used as a training set the other of which is set aside. We define a classifier (e.g., K-nearest neighbor, decision tree, margin-based classifier or other) using the training subset and at least one of the features (or subsets of two or more features in combination). We apply the classifier to a subset of samples. A filter is applied to the performance of the classifier on the sample subset and the at least one feature is added to a "filtered feature list" if the classifier performance passes the filter. We do this for many different realizations of the separation of the development sample set into two subsets, and, for each realization, different features or sets of features in combination. After all the iterations are performed the filtered feature list is used to either select features, or deselect features, for a final classifier.

24 Claims, 8 Drawing Sheets

(56) References Cited

U.S. PATENT DOCUMENTS

| | | | |
|---|---|---|---|
| 2013/0344111 A1* | 12/2013 | Roder | G01N 33/57438 424/274.1 |
| 2014/0188845 A1 | 7/2014 | Ah-Soon | |
| 2015/0102216 A1 | 4/2015 | Roder | |
| 2015/0178639 A1* | 6/2015 | Martin | G06N 20/00 706/12 |
| 2016/0163522 A1 | 6/2016 | Roder | |

OTHER PUBLICATIONS

Chen et al., "Gene Expression Patterns in Human Liver Cancers", The American Society for Cell Biology, Molecular Biology of the Cell vol. 13, 1929-1939, Jun. 2002. (Year: 2002).*

International Preliminary Report on Patentability for PCT application No. PCT/US2016/026046 (filing date Apr. 5, 2016) dated Nov. 9, 2017.

Written Opinion and International Search Report for corresponding PCT application No. PCT/US16/26046 dated Aug. 16, 2016.

Abeel et al., "Robust biomarker identification for cancer diagnosis with ensemble feature selection methods" Bioinformatics 2010 26(3):392.

Der, et al., "Validation of a Histology-Independent Prognostic Gene Signature for Early-Stage, Non-Small-Cell Lung Cancer Including Stage IA Patients" J Thorac. Oncol. 2014 9(1): 59.

Johnson, WE, Rabinovic, A, and Li, C (2007). Adjusting batch effects in microarray expression data using Empirical Bayes methods. Biostatistics 8(1):118-127.

Kimhofer, et al. "Proteomic and metabonomic biomarkers for hepatocellular carcinoma: a comprehensive review", British Journal of Cancer 2015 112:1141.

Saeys, et al.., "Robust Feature Selection Using Ensemble Feature Selection Techniques" Machine Learning and Knowledge Discovery in Databases, Lecture Notes in Computer Science vol. 5212 (2008) p. 313.

Samee et al., "Detection of biomarkers for hepatocellular carcinoma using hybrid univariate selection methods" Theoretical Biol. and Med. Modelling 2012 9:34.4.

Singal, et al., "Meta-analysis: Surveillance With Ultrasound for Early-stage Hepatocellular Carcinoma in Patients with Cirrhosis Ailment" Pharmacol. Ther. 2009 30(1): 37.

Tusher et al., "Significance analysis of microarrays applied to the ionizing radiation response" Proc. Natl. Acad. Sci. USA 2001 98(9):5116.

Witten et al., "Testing significance of features by lassoed principal components" Ann. Appl. Stat. 2008 2(3):986.

Zhi-Zhou, "Ensemble Methods Foundations and Algorithms", CRC Press (2012) p. 70.

Zhou et al., "Regularization and variable selection via the elastic net" J. R. Statis. Soc. Ser. B 2005 67:301.

Zhu, et al., "Prognostic and Predictive Gene Signature for Adjuvant Chemotherapy in Resected Non-Small-Cell Lung Cancer" J. Clin. Oncol. 2010 28(29):4417.

* cited by examiner

Fig. 4

Development Sample Set Realizations

| | Train | Remainder - Set Aside |
|---|---|---|
| Realization 1 | $S_1, S_3, S_5, ...$ | $S_2, S_4, S_6, ...$ |
| Realization 2 | $S_1, S_2, S_5, S_6, ...$ | $S_3, S_4, S_7, S_8, ...$ |
| Realization 3 | $S_1, S_2, S_3, S_7, S_8, S_9, ...$ | $S_4, S_5, S_6, S_{10}, S_{11}, S_{12}, ...$ |
| Realization 4 | $S_1, ... S_{10}$ $S_{21}, ... S_{30}, ...$ | $S_{11}, ... S_{20}$ $S_{31}, ... S_{40}, ...$ |
| ⋮ | ⋮ | ⋮ |
| Realization M | $S_1, ... S_{N/2}$ | $S_{N/2+1}, ... S_N$ |

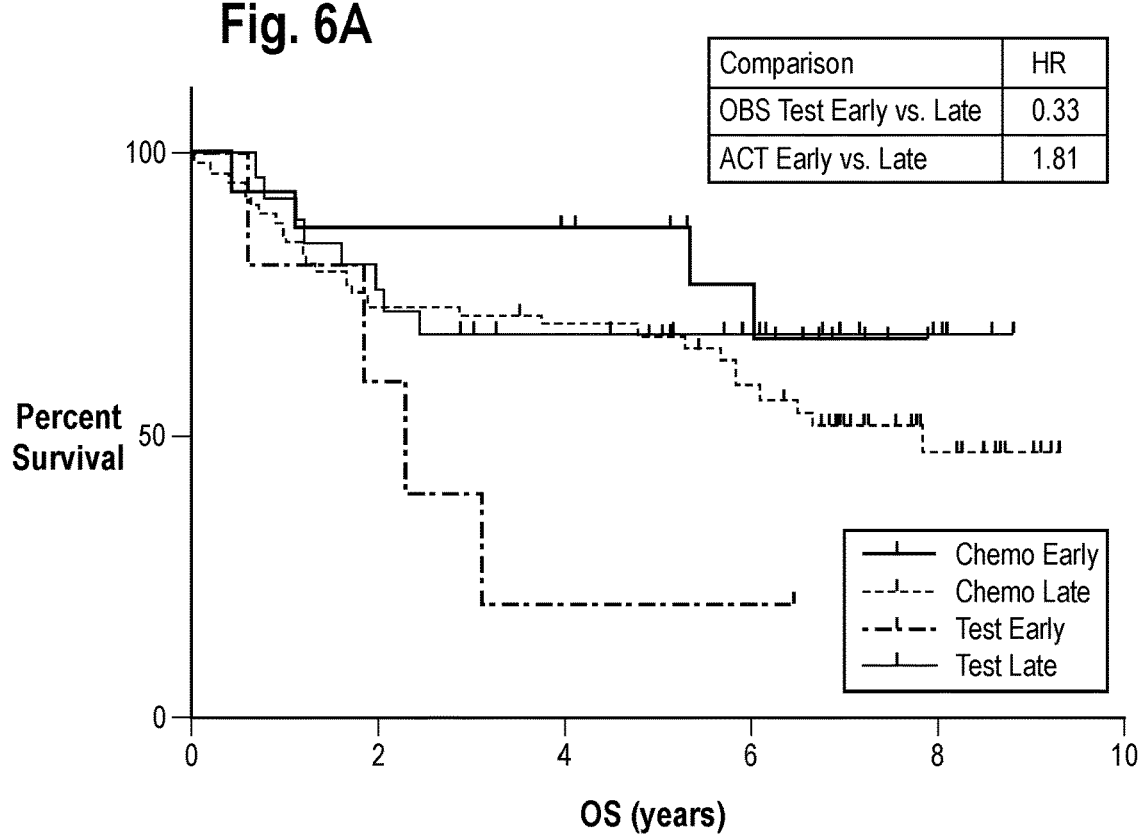
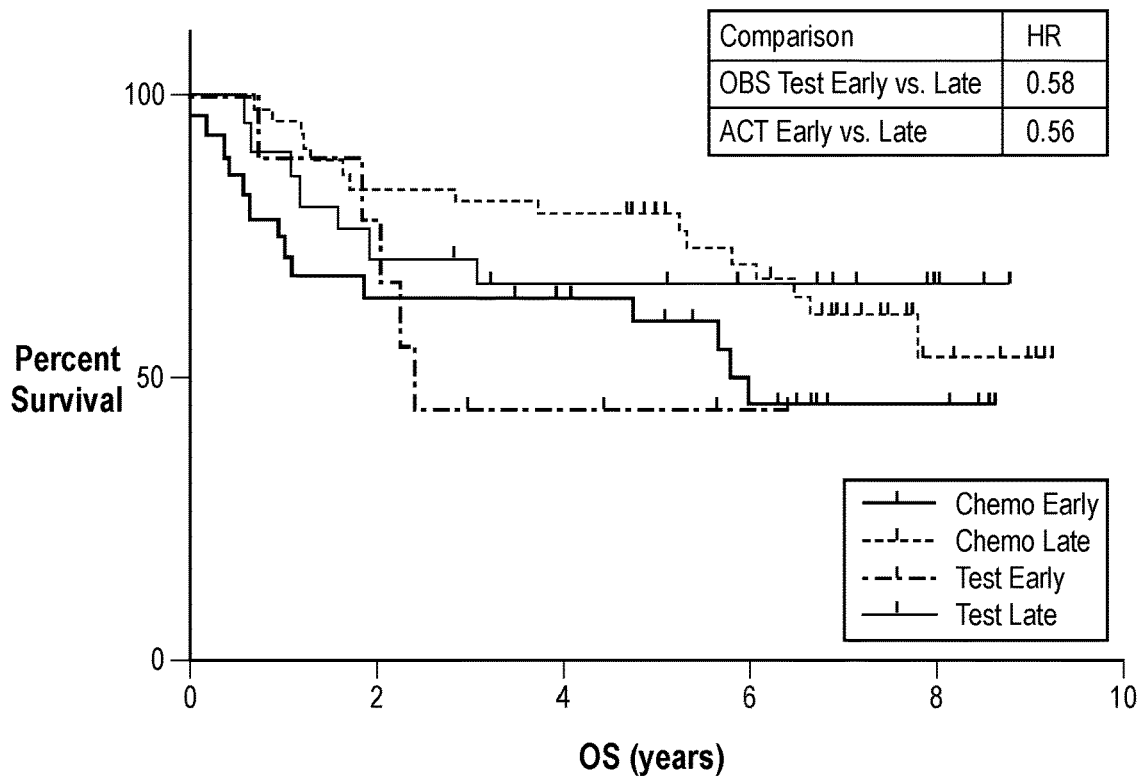

BAGGED FILTERING METHOD FOR SELECTION AND DESELECTION OF FEATURES FOR CLASSIFICATION

PRIORITY

This application claims priority benefits to U.S. provisional application Ser. No. 62/154,844 filed Apr. 30, 2015, the content of which is incorporated by reference herein.

FIELD

This disclosure relates generally to the fields of machine learning and biomarker discovery, and more particularly to a method for selecting or deselecting features in a dataset to improve the performance of a computer-implemented classifier programmed to classify samples, e.g., biological samples.

BACKGROUND

To make classifiers and to identify biologically relevant biomarkers, it is often necessary to be able to identify the most relevant expression measurements (i.e., features) from a dataset of many, possibly thousands of variables measured for tens or hundreds of samples, each of which is associated with clinical data. Such features can take the form of the intensity of peaks in mass spectral data, or genomic data, such as mRNA transcript expression data for hundreds or thousands of genes, or proteomic data such as protein expression levels for a multitude of proteins.

One approach to classifier development, which we have termed "combination of mini-classifiers with dropout" or "CMC/D", is described in our prior U.S. patent application Ser. No. 14/486,442 filed Sep. 15, 2014, the content of which is incorporated by reference herein. Generally speaking, classifiers developed in accordance with the '442 application are able to work well without the need to select only a few most useful features from a classifier development data set. However, at some point the performance of even the methods of the '442 application can degrade if too many useless or noisy features are included in the set of features used to develop the classifier. Hence, in many classifier development and biomarker identification situations it is essential to be able to either select relevant features or deselect irrelevant features.

It should be noted that feature selection and deselection are not simply the complement of each other. Feature selection involves selecting a few features that are statistically significantly correlated with a clinical state or clinical outcome. Feature deselection removes noisy features or features that show no indication of power to classify into the clinical groups. Hence, the latter is not related to an established level of statistical significance of correlation of a feature with clinical state or outcome.

Many methods for feature selection or deselection have been proposed and used in practice. Student t-tests, Wilcoxon sum rank (Mann-Whitney) tests, significance analysis of microarrays ("SAM") (see Tusher et al., "Significance analysis of microarrays applied to the ionizing radiation response" Proc. Natl. Acad. Sci. USA 2001 98(9):5116), and adaptations of logistic regression, including lasso and elastic net (see Witten et al., "Testing significance of features by lassoed principal components" Ann. Appl. Stat. 2008 2(3): 986, Zhou et al., "Regularization and variable selection via the elastic net" J. R. Statis. Soc. Ser. B 2005 67:301), mutual information, and combinations of these methods (see Samee et al., "Detection of biomarkers for hepatocellular carcinoma using hybrid univariate selection methods" Theoretical Biol. and Med. Modelling 2012 9:34.4), have been used to identify features showing differential expression between sample sets representing two known classes. To identify features relevant for the prediction of time-to-event outcomes or classification into groups of patients with better or worse time-to-event outcomes, Cox regression of features to outcome data can be used. See Zhu, et al., "Prognostic and Predictive Gene Signature for Adjuvant Chemotherapy in Resected Non-Small-Cell Lung Cancer" J. Clin. Oncol. 2010 28(29):4417.

Often these methods are applied to data from a development set of samples. As used in this document, a "development set of samples", or simply "development set" refers to a set of samples (and the associated data, such as feature values and a class label for each of the samples) that is used in an exercise of developing a classifier. Often, there are many features (typically several hundred to tens of thousands) measured for each sample in the development set, many more than the number of samples in the development set (typically of the order of 10-100 samples). Applying these methods to the development set of samples can lead to overfitting, i.e. features are selected which demonstrate significant expression differences between classes in the particular development set, but which do not generalize to other sample sets, i.e. in other sample sets different sets of features would demonstrate significant expression differences. This is a recognized problem in feature selection. Ensemble methods (bagging) have been suggested to deal with this issue in feature selection and biomarker identification. Saeys, et al., "Robust Feature Selection Using Ensemble Feature Selection Techniques" Machine Learning and Knowledge Discovery in Databases, Lecture Notes in Computer Science Volume 5212 (2008) p. 313; Abeel et al., "Robust biomarker identification for cancer diagnosis with ensemble feature selection methods" Bioinformatics 2010 26(3):392.

Some methods of feature selection are quite limited in the way that the relevance of features is assessed. One may be interested in identifying features which can be used to classify samples accurately into the defined classes or groups with significantly different outcomes, but determining features where the mean or median is significantly different between classes does not necessarily mean that the feature is particularly useful for accurate classification. Differences in mean may be due to isolated outlier samples. The significance of differences in median may not give a reliable guide to how well the feature can split the development set into the required classes. In addition, typically it is difficult to use any one method, ensemble-based or other, across multiple biomarker settings (e.g. in classification into two clinical states and to find prognostic classifications based on time-to-event data).

This document describes a method of feature selection or deselection that makes use of an ensemble average ("bagging" in machine learning terms) of the filtering of a classification performance estimate. This method has the usual advantages of an ensemble approach (increasing robustness of (de)selected features, avoiding overfitting) and is flexible enough that it can be easily used for both classification into clinical states (e.g. cancer or no cancer) and classification according to groups based on continuous clinical variables (e.g. % weight loss) and censored time-to-event data, such as overall survival. Most important, this method allows for the tailoring of feature selection and deselection to the specific problem to be solved and provides a simple method to deal with known or suspected confounding factors.

SUMMARY

We have discovered that classifier generation methods are improved by selecting, or deselecting, features which are used for classification based on what we have termed "bagged filtering." In particular, after acquiring a development sample data set (e.g., from performing some physical measurement process on a set of samples), in our method the development sample set is split into two subsets, one of which is used as a training set and the other of which is set aside. We define a classifier (e.g., K-nearest neighbor, decision tree, margin-based classifier or other) and apply the classifier using the training subset and at least one of the features. We apply a filter to the performance of the classifier and add the at least one feature to a "filtered feature list" if the classifier performance passes the filter. We do this for many different iterations or realizations of the separation of the development sample set into two subsets, and, for each realization, for all features or, optionally for combinations of features. After all the iterations are performed we then use the filtered feature list to either select features, or deselect features, for a final classifier generated from the development set of samples. It will be appreciated that the above method is performed in a programmed computer. The resulting programmed computer has an improved ability to function as a classifier, and can be used to classify a new test sample.

In more particularity, in a first aspect we have provided a method for improving the functioning of a computer as a classifier by selecting or deselecting one or more features in a data set for generating the classifier. The method includes the steps of:
- a) obtaining physical measurement data from a development set of samples, e.g., mass spectrometry, genomic or proteomic assay, mRNA expression levels, and a class label for each of the samples in the development set, the physical measurement data comprising a feature value for a multitude of individual features (e.g., mass spectral peaks); and, in a programmed computer performing steps b)-g):
- b) separating the data for the development set of samples into two subsets, one of which is used as a training set;
- c) defining a classifier using the training subset and at least one of the features;
- d) applying the classifier defined in step c) to the training subset;
- e) applying a filter to the performance of the classifier applied in step d),
- f) adding the at least one of the features used in step c) to a filtered feature list if the classifier performance passes the filter step e);
- g) repeating steps b), c), d), e) and f) for different realizations of the separation of the development set of samples into two subsets, and for different one or more features in the set of features; and
- h) using the filtered feature list to either select features or deselect features from the multitude of individual features for use in a final classifier generated from the development set of samples.

One purpose of the bagged filtering process of this disclosure is the deselection of features, that is, to remove features from the available feature space that do not contribute meaningfully, or at all, to classifier performance, i.e., so-called "junky" features. This allows a final classifier generated from the development set of samples, without such junky features, to probe deeper into feature space. It also usually produces a classifier with better performance, i.e., increased predictive power and/or generalizability to new data. Furthermore, prior art approaches, such as using univariate testing (i.e., testing the classification performance of individual features) can result in classifiers that turn out not to be generalizable.

One other purpose of this bagged filtering process is to select features from the feature space which have demonstrated good classification performance, and use such features in a final classifier. For example, with a development set of samples containing say hundreds or even thousands of potential features (mass spectral peak intensities, mRNA transcript expression levels, or other) the filtered feature list may yield 10 or even fewer features which can be used for the final classifier. A final classifier based on the selected features can be, for example, a simple K-nearest neighbor classifier. Alternatively, the selected features can be used as a set of features as input for development of a classifier using our "CMC/D" classifier generation method described in the U.S. patent application Ser. No. 14/486,442, filed Sep. 15, 2014.

The filtering step can make use of a simple filter (e.g., the classifier passes the filter if classification accuracy on the training set is at least a threshold level), or it can be what we have described below as a "compound filter", i.e., a filter which has two or more different filtering criteria and a logical operation, typically AND, between each criterion. Examples are described in detail below. The definition of the filter can take into account particular clinical or therapeutic considerations and the existence of confounding variables. In essence, one can define the parameters of the filter (simple or compound) to tune the filter to particular clinical or therapeutic questions. As one example, the filter includes a performance threshold of a hazard ratio between two classification groups. As another example, the samples are obtained from patients grouped in first and second treatment arm groups. A compound filter could take the form of a filter which includes (1) classification performance in the form of a hazard ratio between two classes in the first treatment arm group, (2) classification performance in the form of a hazard ratio between the two classes in the second treatment arm group, and (3) a logical operator, such as AND, i.e., the feature passes the filter only if both criteria are met. As another example, the compound filter could consist of a classification performance in the form of a hazard ratio between two classes, classification performance on a second set of samples (e.g., samples from healthy patients) and the logical AND operator.

In another aspect, a method of improving the ability of a computer to generate a classifier is disclosed. The method includes steps of
- (a) obtaining a development set of samples;
- (b) conducting at least one physical measurement process on the development set of samples (e.g., mass spectrometry, proteomic assay, genomic assay, or other) and obtaining measurement values;
- (c) supplying the measurement values to a computer;
- (d) with the computer conducting one or more pre-processing instructions on the measurement values;
- (e) storing in the computer a feature table for the samples in the form of a list of features and a measurement value for each of the features for each of the samples;
- (f) with the computer, conducting a bagged filtering process on the features of the feature table over many different realizations of a separation of the development set into subsets and over one or more sets of features to either identify a subset of features which have classification power or identify a subset of features which do not have classification power (i.e., "junky features"); and (g) defining a final classifier identifying (1) a subset of features as a result of the process (f), (2) parameters for a classification algorithm, and (3) a reference set for use with the classification algorithm comprising i) a set of samples from the development set, ii) their associated values for the set of features resulting from process (f) and iii) a class label for each of the samples in the reference set.

In still another example, a programmed computer (FIG. 2, 42) will be described having a memory storing a the definition of filter (FIG. 3, 120) in the form of at least one criterion for classifier performance, and instructions for a central processing unit of the computer 42 for applying the filter to the performance of a classifier defined in the computer operating on many different realizations (FIG. 4) of a separation of a classifier development set into a training subset and a second subset and one or more measurement features of each member in the training subset (see FIG. 3). The memory further stores a filtered feature list listing the measurement features that pass the filter after execution of the instructions.

In still another aspect, a testing method will be described which includes the steps of: (a) assaying a sample from a lung cancer patient for the expression level of a set of genes listed in Table 3 (see Example 2), and (b) in a programmed computer comparing the expression levels to a reference set including expression levels of the same set of genes of step (a) from a multitude of other lung cancer patients with a classifier and generating a class label for the sample.

These and still other aspects of the invention will be described in greater detail in the following detailed description and representative examples.

BRIEF DESCRIPTION OF THE FIGURES

FIG. 4 is an illustration of a set of different realizations of the separation of the development sample set of FIG. 1 into training subsets, step 102 in FIG. 3.

FIGS. 6A-6C are Kaplan-Meier plots showing classifier performance in Example 2 for different choices of features and filters, with FIG. 6A showing performance for a simple filter for a prognostic test, FIG. 6B showing performance for a two-stage compound filter for a prognostic test, and FIG. 6C showing performance for a two-stage compound filter for a predictive test.

DETAILED DESCRIPTION

Figure 1:
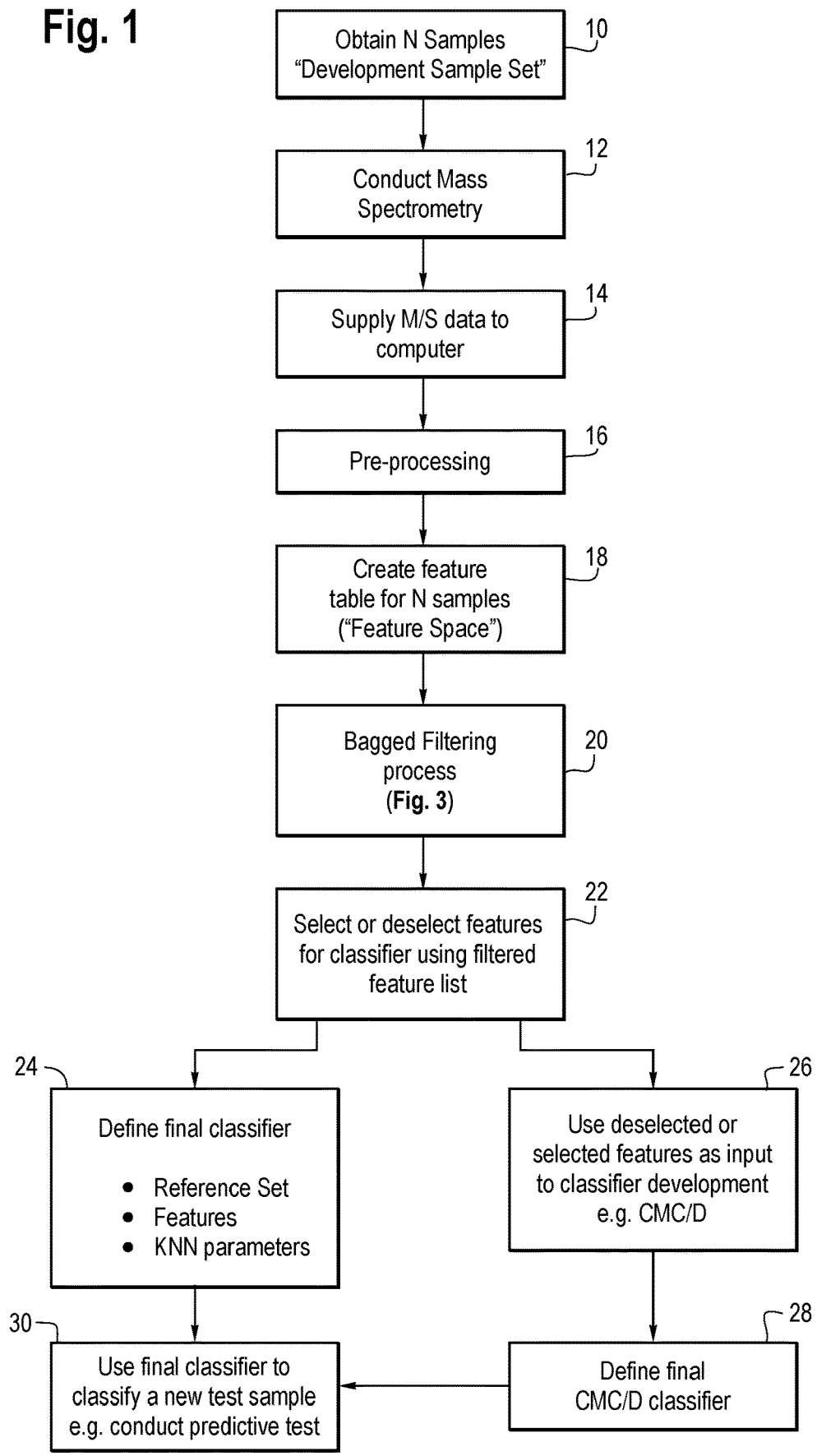
FIG. 1 is a flow chart of a method for generating a classifier from a set of N samples, which includes a sub-step of selection or deselection of features from measurement data of the samples in accordance with the inventive methods of this disclosure.
Figure 2:
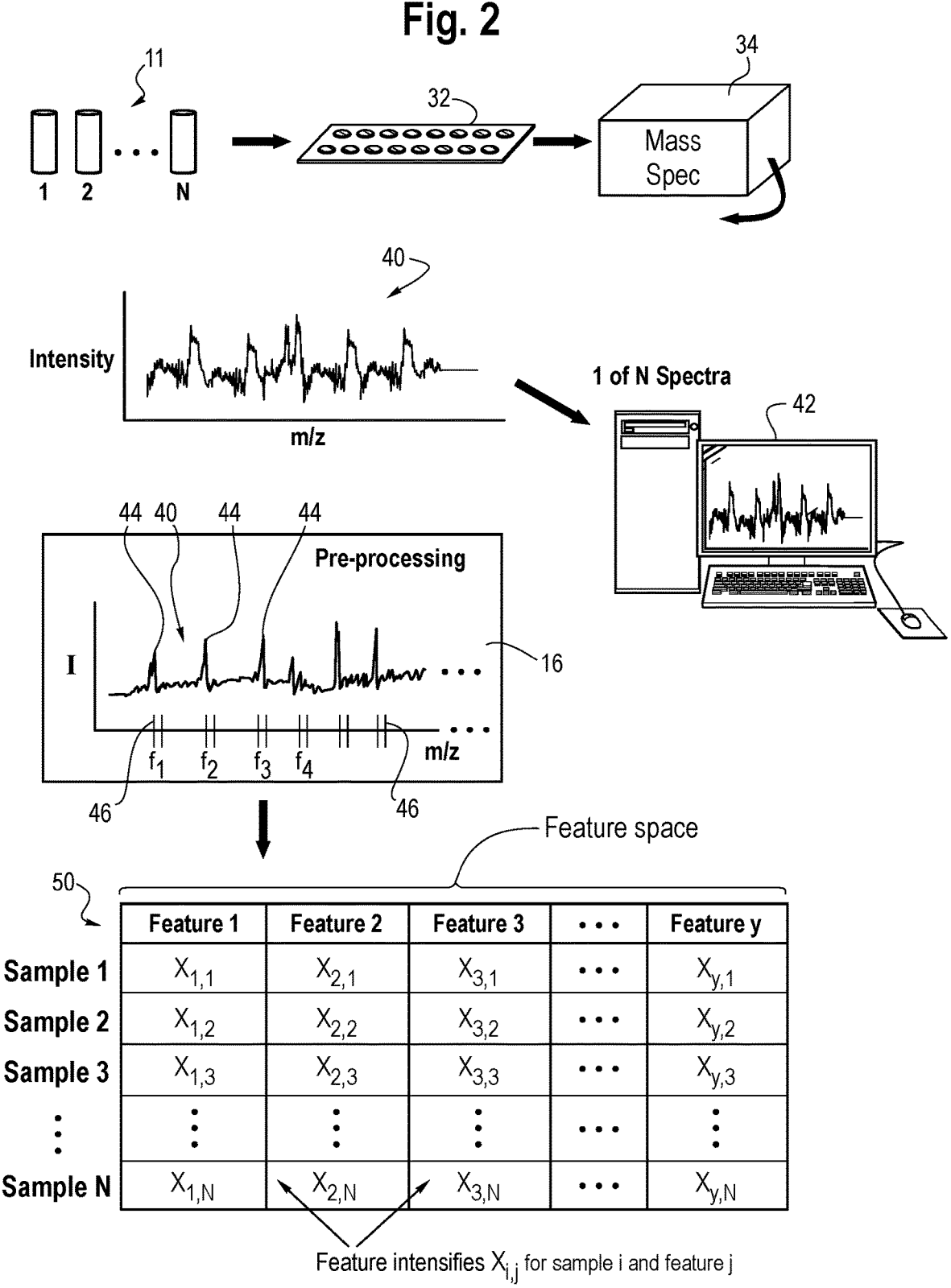
FIG. 2 is a flow chart showing the obtaining of a set of features from measurement data in the process of FIG. 1.

With reference now to FIGS. 1 and 2, a method for improving the ability of a computer to generate a classifier, and selecting and/or deselecting features for use in the classifier will be described. The "bagged filtering" process of this disclosure will be described below in detail in conjunction with FIG. 3. FIGS. 1 and 2 explain the context of how the bagged filtering process can be used in an overall process for generating a classifier, for example, from biological sample data.

In FIGS. 1 and 2, the process begins at step 10 with the obtaining of a set of N samples 11. The type of samples which could be used in this method is not particularly important and could consist for example of tissue or biological fluids, e.g., blood, tumor tissue, etc. In the example of FIGS. 1 and 2 the samples 11 are blood samples, e.g., serum or plasma, from a multitude of different human patients. In one possible and non-limiting example, the patients are enrolled in a clinical trial for safety or efficacy of a particular drug or combination of drugs. Another example is that the samples are from a population of people at high risk of developing a disease. The result of the process of FIG. 1 is a test (implemented in a computer) which can predict whether a patient is a member of a class of patients that is likely or not likely to benefit from the drugs or is likely or not likely to develop or have the disease. The methods of this disclosure improve the functioning of the computer to make this prediction.

At step 12 of FIG. 1, a physical measurement process is carried out on the biological samples obtained at step 10. In one possible example, this measurement process is MALDI-TOF (Matrix Assisted Laser Desorption and Ionization Time of Flight) mass spectrometry. The samples could also be subject to two or more different measurement processes, e.g., mass spectrometry and genomic or proteomic assay, etc. (It will be noted that the use of two different samples from a single patient for measurement is considered equivalent to two measurements of the same physical sample.) As shown in FIG. 2, aliquots of the plasma or serum samples are spotted onto one or more spots of a MALDI-TOF plate 32 and the plate 32 is inserted into a MALDI-TOF mass spectrometer 34. Mass spectrometry is performed on the aliquot(s) and the resulting mass spectrum (or spectra) are generated and stored in the MALDI-TOF mass spectrometer 34. In one possible embodiment this step could take the form of acquisition of Deep MALDI spectra in accordance with the teachings disclosed in U.S. patent application Ser. No. 13/836,436 filed Mar. 15, 2013, now U.S. Pat. No. 9,279,798, the content of which is incorporated by reference.

At step 14 of FIG. 1, the mass spectrometry data obtained at step 12 is supplied to general purpose computer 42 (FIG. 2) equipped with software (known) for analyzing and displaying the spectra. One such spectrum is shown in FIG. 2 at 40, which consists of a plot of intensity (I) as a function of mass/charge ratio (m/z) as is conventional in the art. Spectrum 40 (or a multitude of spectra) are obtained from each sample and supplied to the computer 42.

At step 16, a pre-processing step is performed in the computer 42 of FIG. 2. The pre-processing includes an averaging function to produce a single average spectrum from a multitude of spectra obtained from each sample. The pre-processing also identifies peaks in the spectra which may be useful for classification, and obtains integrated intensity values of m/z ranges associated with such peaks. The pre-processing can include steps of background subtraction, normalization of spectra, and alignment of spectra in order to result in a spectrum for use to identify peaks and measure intensity of features or peaks in the spectra. Such pre-processing is known in the art and described in U.S. Pat. No. 7,736,905, the content of which is incorporated by reference herein. In FIG. 2, such peaks or features in the spectrum 40 are shown at 44. The m/z ranges are shown at 46 for each of such peaks. These m/z ranges correspond to a number of different features $f_1, f_2, f_3, \ldots f_y$. The number of features, y, which are potentially useful for generating a classifier, could be on the order of 50, 100 or potentially much larger, such as 500 or more using the techniques of the Deep MALDI application described above.

At step 18 of FIG. 1, the pre-processing step 16 obtains integrated intensity values for the m/z range 46 for each of the features $f_1, f_2, f_3 \ldots f_y$ and stores this information in a table 50, shown in FIG. 2, of intensity value for each feature. Such a table 50 includes the integrated intensity values for each feature for all N samples in the development sample set 11 of FIG. 2. The collection of features is sometimes referred to as "feature space" in the following discussion.

Figure 3:
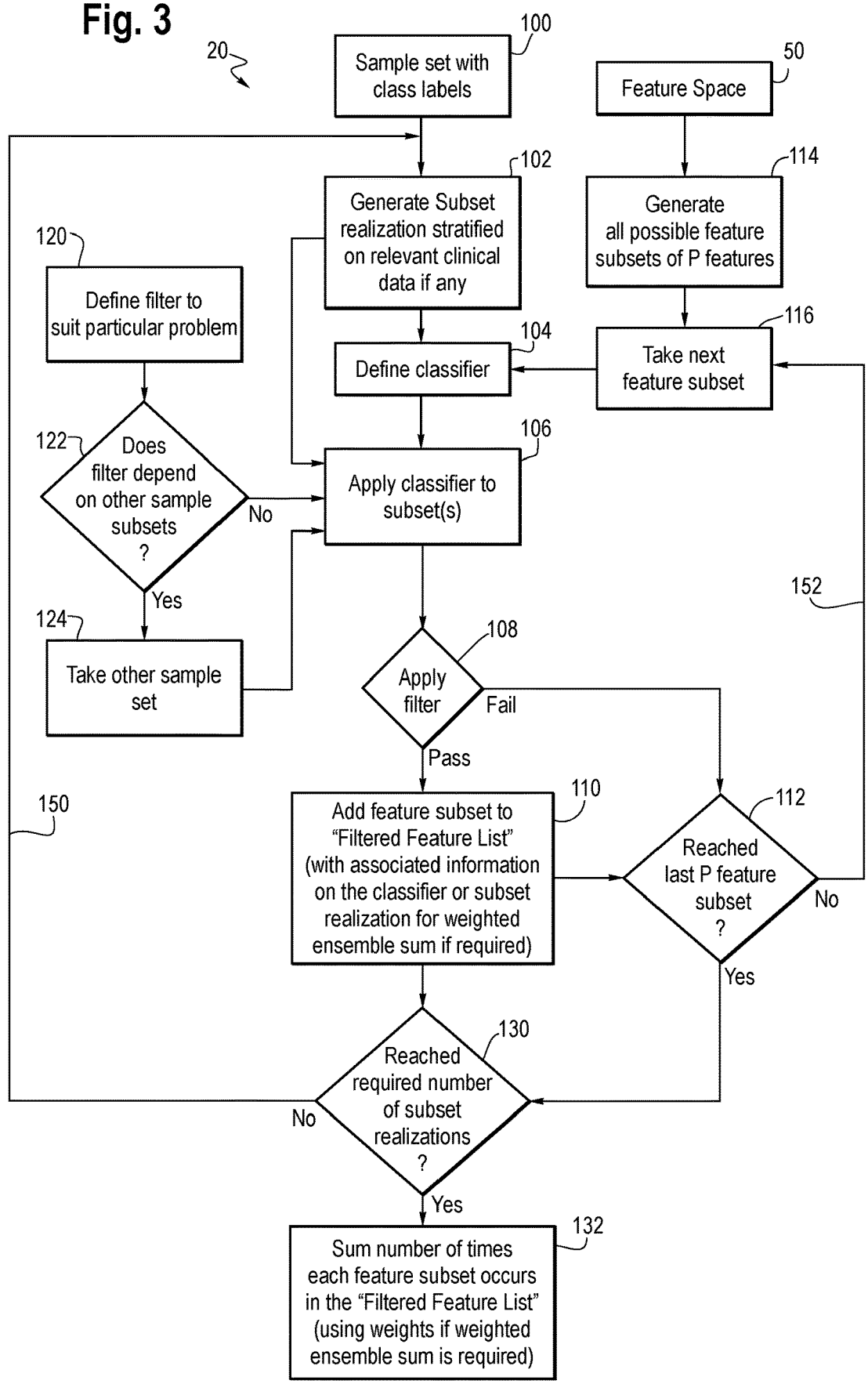
FIG. 3 is a detailed flow chart of the bagged filtering sub-step of FIG. 1.

With reference again to FIG. 1, the problem in classifier development is to identify which of the features $f_1, f_2, f_3 \ldots f_y$ obtained from the samples are in fact useful for creating classifiers which generalize well, and/or to identify which features are "junky" and do not contribute in any significant way to classifier performance. The bagged filtering process 20 of FIGS. 1 and 3 is designed to identify such useful features and/or such "junky" features. This process 20 is a method of feature selection or deselection that makes use of an ensemble average ("bagging" in machine learning terms) of the filtering of a classification performance estimate over many different splits or realizations of the development sample set. This method has the usual advantages of an ensemble approach (increasing robustness of (de)selected features, avoiding overfitting) and is flexible enough that it can be easily used for both classification into clinical states (e.g. cancer or no cancer) and classification according to groups based on continuous clinical variables (e.g. % weight loss) and censored time-to-event data, such as overall survival. Most important, this method allows for the tailoring of feature selection and deselection to the specific clinical problem which is solved and provides a simple method to deal with known or suspected confounding factors. This process 20 will be described in great detail below.

Referring still to FIG. 1, the output of the process 20 is a filtered feature list (see FIG. 7, 70) and statistics of the features that pass a filtering step, such as sums of the number of times a feature subset occurs in the filtered feature list, or a weighted sum as explained below. This list, and statistics, is then used at step 22 to either select or deselect features for a final classifier. Step 22 can be performed automatically in a computer or by a human operator. There are several possible ways in which a final classifier can be defined from the selected features or without the deselected ("junky") features. In one example, at step 24 a final classifier is defined from a set of features selected at step 22 (See FIG. 7), a set of k-nearest neighbor (KNN) classifier parameters and associated program code implementing the KNN algorithm (known), and identification of a reference set to use in the KNN classifier, such as a subset or all of the samples in the development set of samples. Alternatively, at step 26 a set of features (or all the features $f_1, f_2, f_3 \ldots f_y$ minus a deselection of junky features) can be used as input to a new classifier development exercise, such as the CMC/D classifier development method as described in our prior U.S. patent application cited previously. Example 3 below explains this alternative. The result of step 26 is a final classifier which is defined at step 28 in accordance with the procedure of step 26, e.g., as described in the prior CMC/D patent application. At step 30, this final classifier defined at either step 24 or step 28 is then used to classify a new test sample, e.g., as a predictive or prognostic test. The test sample is subject to the same measurement and pre-processing process(es) (e.g., mass spectrometry and mass spectrum pre-processing as explained above) as the development sample set and the sample is then classified by comparison of the selected features in the spectrum to the same features of the reference set in accordance with the classification algorithm of the final classifier. This test can be conducted as a fee for service, e.g., by a laboratory offering sample testing services. In one typical embodiment, this test sample is a blood-based (serum or plasma) sample from a patient with a disease, such as a cancer patient. The test can be whether the patient is likely or not likely to benefit from a particular drug or combination of drugs, is at high risk of development of a disease, to predict overall survival, or answer some other clinical question that is answered by the classifier that is defined using FIG. 1.

Referring now to FIG. 3, as inputs to the bagged filtering process 20 we have the development sample set data 100 obtained as described in FIGS. 1 and 2. Each of the N samples is assigned a class label, e.g., by a human operator after consideration of clinical or outcome data for the patient associated with the sample. The class label can be such as "cancer", "no cancer", "benefit" (i.e., benefited from a particular drug), "non-benefit", "early" (early relapse after commencement of treatment), "late" or otherwise, the particular choice of a moniker for the class label not being important. The "feature space" 50 consists of the set of y features in the measurement data, see FIG. 2. A third input to the process 20 is the definition of a filter which is applied to classifier performance to test whether the particular feature, or set of features, used in each iteration of the flow chart of FIG. 3 met a standard or threshold of performance. The definition of the filter in step 120 is described in considerable detail below and in two examples later in this document. As shown at block 122, the definition of the filter may possibly make use of other sample subsets or measurements, and if so in block 124 these other sample subsets or measurements are obtained so that they can be used with the filter, defined at step 120, in step 106.

Referring still to FIG. 3, at step 102 we generate a split of the development set of available samples (10, FIG. 1, and 11 FIG. 2) into two subsets. See FIG. 4. One of the subsets is used for feature selection and deselection and classifier training (FIG. 4), and the remainder is left aside. If the problem has known confounding variables or there are particular characteristics that need to be taken into consideration, the split into two subsets can be done in a stratified manner. For example, suppose there is a known prognostic factor, such as performance status for lung cancer. It would be good to make sure that all the subsets contain representative proportions of patients in each performance status category. In this way, the final choice of (de)selected features, and any test or classifier built from it, will be well-tuned to the relative proportions of performance status categories expected in the target population. This is of additional importance when there is a factor that can act as a confounder for the clinical test to be created. If one were constructing a prognostic classifier for lung cancer that would add information to existing prognostic factors, and some realizations had random, strong imbalances between classes in performance status, the feature filtering for these realizations would tend to select features associated and correlated with performance status instead of features that are indicative of prognosis independent of performance status. So, some of the realizations would produce suboptimal sets of filtered features and the final choice of selected or deselected features could be correspondingly suboptimal. As shown by the loop 150, this splitting of the development set of samples into two subsets is performed many times, resulting in many different realizations of the separation of the development set of samples into training and remainder subsets.

One example of the separation of the development set of samples into two subsets is illustrated in FIG. 4, showing a first realization 102A, a second realization 102B, etc. up to realization M, 102M. M may for example be 100, 200 or more, depending on the number N of samples in the development sample set, and is typically greater than N. In the first iteration of the loop 150, realization 1 (102A) is created in which the set of N samples $S_1, S_2, S_3, \ldots S_N$ is separated into a training subset 200 consisting of the odd-numbered samples $S_1, S_3, S_5 \ldots$ and the remaining even numbered samples are set aside. The second iteration through the loop 150 results in a different realization 102B of the separation, in this example the training sub-set consists of samples $S_1, S_2, S_5, S_6, \ldots$ while the remainder subset consists of samples $S_3, S_4, S_7, S_8, \ldots$ . The subsequent iterations result in realizations 3, 4, . . . M for M different iterations through the loop 150, as shown in FIG. 4. The aim is to explore the possible variety of subset realizations that can be drawn from the development sample set, so that it is possible to robustly select features over the whole ensemble and avoid overfitting the selected or deselected features to peculiarities of a particular sample set realization. Hence, the precise manner or algorithm by which the realizations are defined is not particularly important. However, in one possible embodiment a stratification of the samples may be performed in the generation of the realizations.

At step 104, a classifier is defined. This step can be simply defining the parameters for a KNN classification algorithm, such as values for k, identification of the realization of the training subset 200 to be used as a reference set, and the identification of one or more features or sets of features in feature space to be used for the KNN classification algorithm. It will be noted in FIGS. 1 and 2 that the feature space 50 can be composed of a large number of features, potentially in the hundreds or even thousands. In the process of FIG. 3, a step 114 is performed in which a list of all possible feature subsets of the features in the feature space is generated. This could be just a list of individual features, or a list of the individual features plus all possible pairs of features, or all possible sets of n different features wherein n<y (e.g., some integer such as 2, 3 or 5), or otherwise. At step 116 in the first iteration, one of the feature subsets is selected. For purposes of example, the first feature $f_1$ in the spectrum of FIG. 2 is selected and the classifier definition step 104 identifies or flags feature $f_1$ to use in the classification algorithm.

It will be noted that the present discussion and the following examples use simple k-nearest neighbor (KNN) classifiers. However, the type of classifier used is not important, and any type of classifier that can be trained on the single feature using the given subset of sample data can be used.

At step 106, the classifier defined at step 104 is applied to the training subset (200 in FIG. 4), and possibly also to other sets of samples where the class labels are known (124 in FIG. 3), and the classifier performance is assessed. The performance of the classifier can be evaluated in terms of accuracy (sensitivity and/or specificity) or in terms of any other metric that can be defined using the available clinical data for the samples. For example, if the aim is to identify patients likely to have good or poor survival on a particular treatment regimen, the performance of the classifier could be assessed in terms of the hazard ratio (HR) between the resulting classification groups or the difference in medians of the resulting classification groups.

At step 108, a filter (defined at step 120) is applied to these performance estimates generated at step 106, such that the feature selected at step 116 only passes filtering if the classifier using this sample subset for training has adequate performance. The filter may be simple, such as demanding a minimal level of classification accuracy on the given training subset of samples, or may be compound, composed of any logical combination of criteria. As an example of a compound filter, if a classifier is required that is predictive of differential survival between two treatments, the filter could be a logical AND between a hazard ratio (HR) between the two classes in one treatment group that has to be smaller than a set threshold, e.g. 0.5, and a HR between the two classes in the other treatment group that has to be close to 1.0, e.g., greater than 0.75 and less than 1.33. The possibility of creating compound filters allows for the tuning of feature selection to the precise clinical question to be addressed, and this is the main advantage of this method over previously used approaches to feature selection and deselection. If there is a known confounder in a particular sample set, use of a compound filter can help eliminate confounding effects on feature selection and deselection. For example, if a classifier is to differentiate patients with cancer from patients without cancer, but the sample set available for training is plagued by a confounding variable, such that the cancer patients available for study have better liver function than the no cancer patients, standard methods may select features which differentiate between the patient samples according to liver function rather than to presence of cancer. With this new method, a compound filter can be implemented that demands that the feature produces a classifier with a minimal level of accuracy on the training samples and simultaneously classifies a separate set of patients with good liver function and without cancer as having no cancer, not as having cancer. Thus, a compound filter defined in this step can include a criterion of classification performance on a separate sample set, in this example a set of samples from patients with good liver function and no cancer.

At step 110, a "filtered feature list" (FIG. 7, 70) is created based on the results of applying the filter step 108. In the first iteration of the loop 150, if the feature selected at 116 meets the filtering criteria applied at step 108, it is added to the filtered feature list 70, otherwise it is not added. At step 112, for the given realization of the separation of the development set, a check is made to see if the last of the P feature subsets has been reached, and if not the process loops back as shown at 152 and another feature subset (such as the second feature $f_2$ in the list of features) is selected at step 116 and the steps 104, 106, 108, 110 and 112 are repeated. The process continues until the last feature(s) in the feature subset defined at step 114 is reached. At this point, the process proceeds to step 130 and a check is made to see if the required number of subset realizations (see FIG. 4) has been reached, and if not, the process loops back as indicated by 150 to step 102 and another subset realization is generated, such as realization #2 102B in FIG. 4.

The process proceeds into a second iteration of the loop 150, in which steps 102, 104, 116, 106, 108, 110 and 112 are performed. This next iteration results in possible inclusion of the feature(s) used in the iterations to the filtered feature list 70 created at step 110.

At step 132, after all the required subset realizations (102M, FIG. 4) have been subject to the process of FIG. 3 the filtered feature list 70 is then analyzed. In particular, a sum is performed of the number of times each feature subset (single features 72 (FIG. 7), ordered pairs of features 74, triplets of features 76, etc.) appears in the filtered feature list. This summing can be performed using weights if a weighted ensemble sum is required. The sums generated at step 132 can then be used to select, or deselect features, when generating or defining a final classifier from the development sample set.

To explain this aspect in more detail, all features that pass filtering for a given training subset are added to the filtered feature list 70 at step 110. This filtering for all features is repeated for all the subset realizations generated (each iteration of loop 150). The lists of features passing filtering are then compiled across the subset realizations (FIG. 4) to determine how often a feature passes filtering. In a possible extension of the method, instead of just summing how often a feature passes filtering, a simple ensemble average, a weighted sum could be used, in the spirit of weighted ensemble averages used for classification. This step may optionally make the use of the techniques described in Zhi-Zhou, "Ensemble Methods Foundations and Algorithms", CRC Press (2012) p. 70, which is incorporated by reference. The weights would be computed based on some property of the subset realizations, possibly in combination with the feature being considered. For example, one could weigh the features passing the filter with a function of a diversity measure of the classifier. This could be particularly useful when a large number of subset realizations produce essentially similar classifiers. This is the case when the subset realizations show little diversity. The large number of essentially identical classifiers will produce very similar lists of feature subsets that pass filtering and these will tend to completely outweigh the feature subsets produced from the smaller number of realizations which lead to classifiers that classify the training set samples differently. To appropriately make use of the information from the minority of realization subsets that provide the diversity, one would need to weigh the sum so that the majority does not always dominate. This must be carried out carefully to avoid removing the benefits of bagging. For example, suppose that more than half of the subset realizations produced classifiers with almost identical classifications which lead to identical features passing filtering for more than half of the subset realizations. This repeated list of features could be weighted with a factor less than other feature lists passing filtering produced, e.g. a factor of 2 or more smaller, so that the features which pass filtering over other subset realizations have a chance to be selected or avoid deselection.

Features that pass filtering for most of the training subsets are likely to be useful and robust for the clinical question being addressed by the classifier, as they are not dependent on any particular realization of the training set. Features that pass filtering for very few training subset realizations are likely to have been overfitted to those few subsets and are not likely to be useful. For feature deselection, features can be deselected if they pass filtering in fewer than a specified number or percentage of training subset realizations (FIG. 4). For example, features that pass filtering in less than, e.g., 10% or 25% of the training subset realizations could be considered very unlikely to contain information relevant to the problem in question and could be eliminated from the feature set used to make a classifier or test, for example, as defined in step 24 of FIG. 1 or as used for classifier generation by the method of CMC/D in step 26 of FIG. 1.

For feature selection, features can be selected if they pass filtering in more than a specified number or percentage (e.g., 75% or 90%) of training subset realizations. Depending on how tightly one specifies the filter definitions, the feature selection can result in the selection of a small number of features to use in a final classifier, such as 10 or less, even when each sample in the development set contains measurement data for hundreds or even thousands of features, as illustrated in Examples 1 and 2. It is also possible for the filtered feature list (FIG. 7) after the conclusion of the process of FIG. 3 to include a fairly large number of features, say 50 or 100, and the designer can specify that the top 5 or 10 features are used in the final classifier defined at step 24 of FIG. 1, and then test that classifier on an independent validation sample set and see how it performs and if necessary either augment or reduce the number of features used in a final classifier.

The advantages of this method are multiple. The bagged nature of the method, combining information on which features pass filtering across the multitude of subset realizations (FIG. 4), minimizes the possibility of overfitting by the selection of features that produce very good classification on one sample set but do not generalize to other sample sets. This may be particularly vital when selecting very few features from a very large number of possible features using a small development set, which is typically the case in problems using mRNA datasets. The use of the filtering allows one to pick features based on the particular question for which they are of interest. It easily allows the selection of features likely to be useful for a predictive test rather than a purely prognostic test. It can be extended to many metrics for classifier performance other than accuracy, for example, measurements based on time-to-event data (Hazard Ratio (HR), medians, difference of medians, ratio of HRs) or unconventional endpoints (e.g. difference in median percentage weight loss or difference in mean decrease in cholesterol levels between classes). If there are known confounding factors or constraints on performance, the flexibility of filter creation provides a way to take account of these, e.g., features that differentiate between patients with better and worse outcomes for breast cancer therapy, but which are not surrogates for age or menopausal status (important as post-menopausal patients generally have better outcomes than pre-menopausal patients).

As a further variation of the method, it would be possible to perform a label flipping for persistently misclassified samples during classifier training (step 106, FIG. 3), and then in a subsequent iteration of the method perform the feature deselection (or selection) with the new training labels, as described above.

The following examples illustrate the advantage of the method for feature selection and deselection in accordance with FIGS. 1-4.

Example 1

Classifier for Early Detection of Hepatocellular Carcinoma (HCC) with Confounder of Liver Function Early detection of hepatocellular carcinoma (HCC) is critical for improving patient prognosis. If hepatocellular carcinoma is detected early, it can be treated by resection or liver transplant, with relatively good outcomes (5 year survival of around 70%). Singal, et al., "Meta-analysis: Surveillance With Ultrasound for Early-stage Hepatocellular Carcinoma in Patients with Cirrhosis Ailment" Pharmacol. Ther. 2009 30(1): 37. However, currently less than 30% of HCC is diagnosed at this stage, with most cases being diagnosed when there are few therapeutic options, none of which offer hope of a good prognosis (5 year survival of around 5%). Id. Many attempts have been made to create multivariate serum tests to detect HCC in the high risk population of patients with underlying liver disease. Kimhofer, et al. "Proteomic and metabonomic biomarkers for hepatocellular carcinoma: a comprehensive review", British Journal of Cancer 2015 112:1141. However, none have yet been successfully validated. One factor that makes this a difficult task is that patients in the high risk screening population have underlying liver disease and display a wide range of impairment of liver function. This variation in liver function is evident in the protein expression levels in serum and can be a confounding factor to robust test development.

For example, a set of serum samples was available for test development where samples were collected from patients at the time of surgery. Some patients were undergoing liver resection or transplant for early stage HCC; other patients, without HCC, were undergoing transplant surgery for underlying liver disease. For patients without HCC to be eligible for liver transplant, liver function must be severely impaired. Therefore the liver function of the patients without HCC was much worse than that of the patients with HCC. If one tries to construct a test for HCC using these samples, it can easily be achieved by measuring liver function: measurement of proteins up- or down-regulated with liver impairment will indicate no HCC, with the converse indicating HCC. While this test would work well on this sample set, it would not work in a real screening population, where patients with all levels of liver function must be screened and all could potentially have HCC. Our novel method of feature selection as explained in this document can be used to select features (expressions of proteins or peptides, or mass spectral peaks corresponding to such proteins or peptides) useful for identifying HCC that are not simply measurements of or surrogates for liver function, and these features can then be used to create a useful test that can generalize to other unconfounded sample sets.

Our pending U.S. application Ser. No. 14/936,847 filed Nov. 10, 2015 (and prior U.S. provisional application Ser. No. 62/086,805 filed Dec. 3, 2014) describes a classifier development from a development sample set in the form of blood-based samples for early detection of HCC in high risk populations. The content of the '847 application is incorporated by reference herein. Deep MALDI mass spectra were acquired from all samples in the development set, 48 from patients with HCC, 53 from patients with underlying liver disease but without HCC, as well as from an additional set of 34 samples from patients with healthy livers. Spectra were pre-processed and 300 features (mass/charge (m/Z) regions in the spectra) were defined. Feature values were obtained for each sample and feature by integrating the intensity of the spectrum across the feature's m/Z region. Feature values were normalized to render them comparable between samples. In addition, for each sample the level of alphafetoprotein (AFP) was also measured. High levels of this protein are known to be indicative of HCC, but a test based solely on AFP lacks sufficient sensitivity and specificity to be clinically useful. Abeel, et al., "Robust biomarker identification for cancer diagnosis with ensemble feature selection methods" Bioinformatics 2010 26(3):392.

The aim was to create a classifier able to discriminate between patients with underlying liver disease with or without HCC. For this study we chose to use a K-nearest neighbor (KNN) classifier with K=7 that would be trained on a subset of the 101 development set samples (from patients with or without HCC all having underlying liver disease). The same training subset (24 HCC samples and 27 no HCC samples) was used for the final classifier for all approaches. The remaining samples in the development set (24 HCC samples and 26 No HCC samples) were held back as an internal validation set for testing the final classifiers.

As with many varieties of classifiers, performance of KNN classifiers can degrade when large numbers of noisy or irrelevant features are added to the classifier. The target for this study was to use a variety of methods to select the best 5 features, from the set of 300 mass spectral features and AFP level, for use in classifiers and compare the performance of the resulting classifiers, including using prior art approaches and the approaches of this disclosure. Thus, in this example the method of FIG. 3 was used for feature selection. To test classifier performance on an independent validation set, spectra were also acquired from samples from a separate cohort of 193 patients with liver disease, 110 with HCC and 83 without HCC. The No HCC patients in this cohort were more representative of a typical population of patients with underlying liver disease, with much better overall liver function. The HCC patients had overall more advanced cancers than the very early stage cancers of the development cohort.

Five approaches were taken to identify the top few features most likely to be useful in classification, with approaches 1-3 representing prior art approaches and approaches 4-5 representing our new approach:

1. Features with lowest p value for a Student t-test between all samples in the development set with HCC vs No HCC.

2. Features with lowest p value for a Wilcoxon sum rank test (Mann-Whitney test) between all samples in the development set with HCC vs No HCC.

3. Results of significance analysis of microarrays (SAM) analysis between all samples in the development set with HCC and No HCC.

4. The novel feature selection method with a simple filter (defined at FIG. 3, step 120) of classification accuracy on the subset realizations (FIG. 4) created from the development set, bagged over all subset realizations. This feature selection was performed using the method of FIG. 3. A final classifier was defined as per step 24 of FIG. 1 using the selected features.

5. The novel feature selection method with a compound filter (defined at FIG. 3, step 120) of classification accuracy on the subset realization, AND accuracy of classification of a set of 17 of the samples from patients with healthy liver as having no cancer, bagged over all subset realizations (FIG. 4) created from the development set. This feature selection was performed using the method of FIG. 3. A final classifier was defined as per step 24 of FIG. 1 using the selected features.

The top features selected for each method are listed in table 1.

TABLE 1

Features selected by each method. Mass spectral features are denoted
by the center of the m/Z defining region (in Daltons).

| Feature selection method | Features selected | Criterion[1] |
|---|---|---|
| 1. Student t-test | 12866, 12965, 13062, 17390, 17601 | $P < 1.00 \times 10^{-9}$ |
| 2. Wilcoxon sum rank test | 8804, 9023, 12965, 17390, 17601 | $P < 1.00 \times 10^{-9}$ |
| 3. SAM | 12866, 14198, 14248, 17390, 18022 | q = 0 and absolute value of score > 3.20 (min (fold change, 1/fold change) < 0.522) |
| 4. Accuracy filter alone* (FIG. 3, step 120) | 5407, 8688, 8804, 9023, 9569, 17390 | Features passing filtering in >197 realizations out of 200 |
| 5. Accuracy filter + filter that healthy liver pts classify as cancer (compound filter defined at FIG. 3, step 120) | 3263, 5222, 5492, 5561, AFP | Features passing filtering in 176 or more realizations out of 200 |

*6 features taken as there was a tie for 5 ranked feature;

[1] criteria selected to produce the features ranked in the top 5 places

Figure 5A:
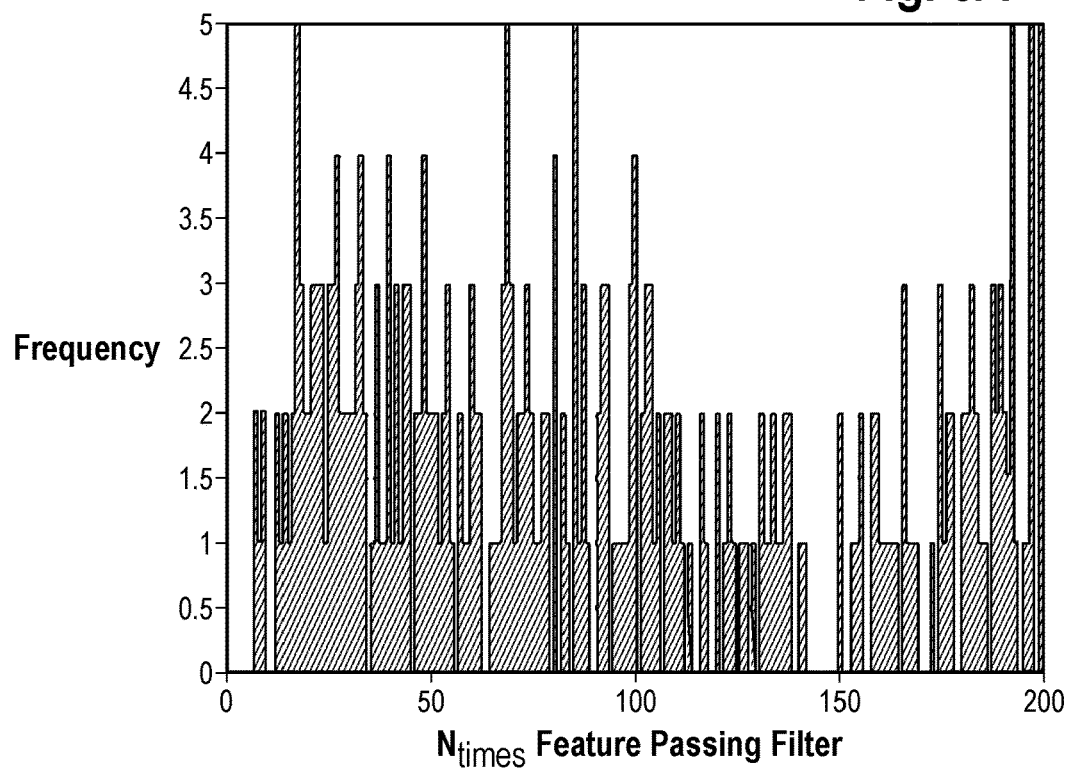
FIGS. 5A and 5B are plots of the frequency of the number of times a feature passes the filtering step using the methodology of FIG. 3 in Example 1, with FIG. 5A a plot for a simple filter and FIG. 5B a plot for a compound filter.
Figure 5B:
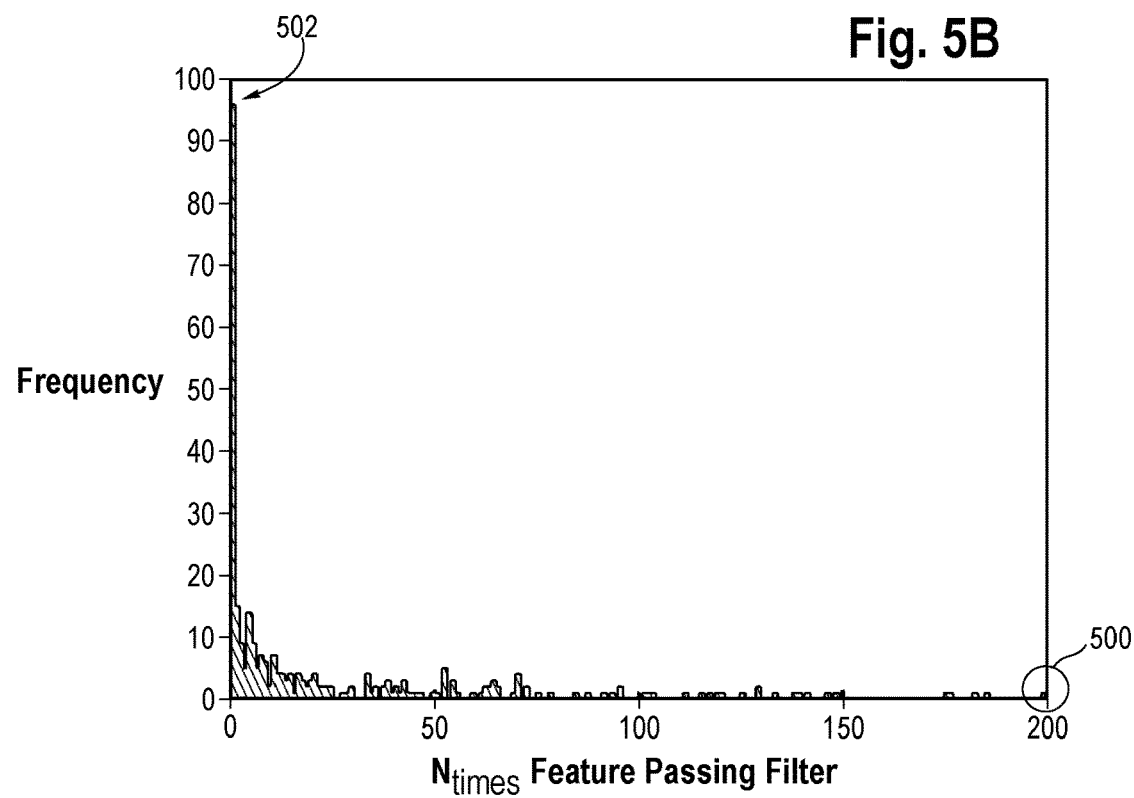

The two bagged (ensemble) feature selection approaches (4. and 5. in Table 1) will now be discussed in more detail. Feature selection followed the methodology of FIG. 3, described at length above. Two hundred training subsets of the 101 development samples were generated (M=200 in FIG. 4). KNN classifiers (K=7) were defined at step 104 with each subset realization of the training set for each of the 301 features, i.e., 301 iterations through loop 152. These 301 KNN classifiers were applied to the training subset 200 (FIG. 4) and the classification accuracy evaluated at step 106. For approach (4.) if the classification accuracy of the training set exceeded 0.70, the feature passed filtering and was added to the filtered feature list. For compound filter approach (5.) the feature passed filtering if the classification accuracy of the training set exceeded 0.55 and at least 12 of the 17 samples from patients with healthy livers selected for filtering were classified as No HCC. The filtering settings were selected so that there was at least one common feature that passed filtering for all realizations. The filtering process was repeated for all features and then this was repeated for all 200 subset realizations. The number of realizations for which each feature passed filtering was calculated at step 132. FIGS. 5A and 5B show histograms of the number of times features passed filtering for approach (4.) (FIG. 5A) and approach (5.) (FIG. 5B). In FIGS. 5A and 5B, the number of times a feature passes filtering is shown on the X axis, and the number of features for which this occurs is shown on the Y axis. Thus, in FIG. 5B there was one feature shown at 500 which passed filtering all 200 times, but the frequency of this occurring was once. This feature was AFP. There were many features which did not pass filtering at least once, indicated by the large bar 502 in FIG. 5B.

There is no apparent structure in the distribution for approach (4.) shown in FIG. 5A. The six features that appeared most often (in more than 197 realizations) were selected. (Six features were selected rather than five due to a tie for 5th rank.) They did not include AFP. In contrast, the distribution for approach (5.) using compound filtering (FIG. 5B) tails off sharply. There are very few features that pass filtering in all or most of the training subset realizations. Notably, there was only one feature that was found to pass compound filtering in all 200 realizations: AFP.

Comparing the features selected by the four approaches (Table 1), it is clear that while the first 4 methods in Table 1 (approaches 1., 2., 3. and 4.) have features in common, and moreover features not appearing in the list for one of the first four methods tend to appear as very highly ranked features outside the top five (data not shown), the feature list for approach (5.) has no features in common with any of the other methods and is the only one to select AFP as a top ranked feature. The Wilcoxon method (approach 2.) ranks AFP 38th ($p=1.2 \times 10^{-6}$), bagged simple accuracy filtering (approach 4.) ranks AFP 41st (passing filtering in 180 of the 200 realizations), SAM (approach 3.) ranks it 134th, and the t-test method (approach 1.) ranks AFP 198th, as not even significantly different between groups (p=0.199). Hence, only approach (5.) with compound filtering as described above manages to clearly recognize the utility of the known biomarker, AFP, from this dataset. That is, ensemble averaging alone does not help in overcoming the confounder, the compound filtering is the essential element.

The performance of the 5 classifiers on the various sample sets are summarized in Table 2. In each case, the final classifier was a simple KNN classifier defined at step 24 of FIG. 1 that uses the features selected and listed in Table 1 for classification.

TABLE 2

Performance of the 5 classifiers on the test and validation sets

| | Test Set HCC accuracy | Test Set No HCC accuracy | "Healthy liver" classification | Validation set HCC accuracy | Validation set No HCC accuracy |
|---|---|---|---|---|---|
| 1. t-test | 14/24 (58%) | 25/26 (96%) | 1/17 No HCC | 83/110 (75%) | 15/83 (18%) |
| 2. Wilcoxon test | 15/24 (63%) | 22/26 (85%) | 0/17 No HCC | 89/110 (81%) | 5/83 (6%) |
| 3. SAM | 12/24 (50%) | 24/26 (92%) | 0/17 No HCC | 75/110 (68%) | 15/83 (18%) |
| 4. Simple filtering | 17/24 (71%) | 21/26 (81%) | 0/17 No HCC | 91/110 (83%) | 4/83 (5%) |
| 5. Compound filtering | 15/24 (63%) | 21/26 (81%) | 17/17 No HCC | 93/110 (85%) | 46/83 (55%) |

All feature selection methods are able to produce classifiers with some power to discriminate between samples from patients with cancer and no cancer within the test set of samples drawn from the development set. However, approach (5.) using compound filtering is the only one that is able to classify samples from patients with healthy livers and no cancer correctly (which it does 100% of the time on the 17 samples not used in filtering or training of the classifier), and that can generalize a level of discriminative power to the independent validation set. As all classifiers apart from that of approach (5.) are unable to classify the samples from patients with healthy liver as cancer-free, it can be inferred that they have not classified the samples based on the expression of proteins indicating presence or absence of cancer, but instead have classified the samples based on the expression of proteins related to the confounding factor of liver function.

This example illustrates the power and versatility of this feature selection method to deal with known confounding factors present in sample sets available for classifier development. Through a simple extension of the filter defined to select useful features, the process we have described in FIG. 3, using the compound filter defined at 120 (approach 5.) takes account of the known confounder to produce a feature set and classifier that can generalize to unseen datasets.

In addition to coping with confounding factors, this method can also enforce constraints that arise in clinical applications. For example, suppose existing prognostic factors are insufficient to allow a physician to provide an accurate prognosis for a patient. A test may be required to provide prognostic information that is complementary to existing factors. Tuning the filtering in feature selection to require that selected features are not surrogates for these known existing factors (e.g. that all older patients are not classified to the "poor prognosis" classification or that all patients with high cholesterol are not classified to the "high risk" group for heart disease related problems) will produce biomarkers or tests that can provide complementary information and better meet the real clinical needs of physicians.

A final classifier for use in conducting early detection of HCC in high risk populations could consist of the features listed in Table 1 for approach (5.), and the parameters for a KNN algorithm using as a reference set for classification a subset of the samples used to train the classifier as described above in our co-pending U.S. application Ser. No. 14/936, 847 filed Nov. 10, 2015. The classifier could be generated using the procedure of FIGS. 1-3 and defined at step 24 in FIG. 1. The classifier feature space includes both mass spectrometry data for the mass spectral features listed in Table 1 as well as AFP expression level measurement for each member of the reference set of samples. To conduct a test on a patient sample, the blood-based sample is subject to mass spectrometry and AFP assay to measure the expression level of AFP. The measurement data is input to the KNN algorithm and the computer implementing the algorithm generates a class label for the sample, such as Cancer or No Cancer. The results are then provided to a physician ordering the test.

Alternatively, one can do a feature deselection from 300 mass spectral features down to 100 mass spectral features and add in AFP as an additional feature in accordance with the process of FIG. 3, and then perform a CMC/D classifier development as per steps 26 and 28 of FIG. 1 to generate a final classifier. See Example 3.

Example 2

Feature Selection in Lung Cancer Genomics—Tailoring a Test to Clinical Need

This example uses publically available mRNA data collected as part of a randomized study of lung cancer treated with or without adjuvant chemotherapy (ACT). Clinical data, including overall survival (OS), and mRNA expression for 62 patients on the observational arm (OBS) and 71 pts on the ACT arm are available within the GEO database. The dataset GSE14814 is available from the NIH.gov website, see our prior provisional application for the link. A study published on this dataset (Zhu, et al., "Prognostic and Predictive Gene Signature for Adjuvant Chemotherapy in Resected Non-Small-Cell Lung Cancer" J Clin Oncol 2010 28(29):4417) has shown that it is possible to make a test that differentiates patients with better and worse outcomes on the OBS arm and indicates that it is possible that the test has predictive value with respect to ACT versus OBS, i.e. the two groups of patients identified by the test have differential benefit from ACT compared with standard care (OBS) without addition of adjuvant chemotherapy. The prognostic power of the test was validated in a separate study on an independent dataset. Der, et al., "Validation of a Histology-Independent Prognostic Gene Signature for Early-Stage, Non-Small-Cell Lung Cancer Including Stage IA Patients" J Thorac. Oncol. 2014 9(1): 59.

To work on this data set, having these two independent datasets available, we chose to first use only probes that were available for both datasets. In addition, mRNA probes measuring the same gene were averaged together. This resulted in a set of 13,194 genes. The datasets were then made comparable using COMBAT, a software tool published by Boston University, Johnson Laboratory. See our prior provisional application for a link related with the COMBAT software. See also Johnson, W E, Rabinovic, A, and Li, C (2007). *Adjusting batch effects in microarray expression data using Empirical Bayes methods*. Biostatistics 8(1):118-127. These data processing steps prior to classifier generation mean that the dataset we work with is not identical to that used in the original article and so differences in details of results may be expected.

For this study, we wanted to demonstrate that it is possible to create two tests with different clinical utility from the same dataset by adjusting the filtering used within the feature (de)selection method: a test prognostic under both treatments, i.e. differentiating between patients with better or worse outcomes independent of therapy and a predictive test under which the patient groups have differential benefit between the two therapies, and in particular one where one group of patients receives benefit from receiving adjuvant chemotherapy while the other group does not.

Tuning of the test to the different clinical requirements (predictive or prognostic test) was achieved using the novel feature selection method described in FIG. 3. The five top-ranked mRNA features (those passing filtering most often across realizations) were selected using three different kinds of filtering (defined at FIG. 3, step 120):

a. Simple Prognostic: A single filter passing only features for which the corresponding KNN (K=5) classifier produced groups within the OBS arm training set with a HR for OS between them in the range 3 and 10.

b. Double Prognostic: A compound filter of a logical AND between
  i. A filter passing only features for which the corresponding KNN (K=5) classifier produced groups within the OBS arm training set with a HR for OS between them in the range 2 and 10, and
  ii. A filter passing only features for which the corresponding KNN (K=5) classifier produced groups within the ACT arm with a HR for OS between them in the range 2 and 10.

c. Double Predictive: A compound filter of a logical AND between
  i. A filter passing only features for which the corresponding KNN (K=5) classifier produced groups within the OBS arm training set with a HR for OS between them in the range 4 and 10, and ii. A filter passing only features for which the corresponding KNN (K=5) classifier produced groups within the ACT arm with a HR for OS in the range 0.75 and 1.33 for OS.

All filtering approaches were bagged over 300 subset realizations in the iterations of FIG. 3 (loop 150). Samples in the OBS arm were sorted according to overall survival (regardless of censoring status). The first 31 samples were assigned to the "Early" (early death) class and the second 31 samples were assigned to the "Late (late death) class. Pairwise in this order, the samples were randomly assigned one to the filtering set and the other to the leave out set (not used for feature selection). This random splitting was repeated 300 times to generate the 300 realizations used for feature selection (FIG. 4).

The filtering approaches (a)-(c) above were used on the realizations and the features that passed filtering for each realization were saved and collated across the realizations. For each approach a filtered feature list was made showing how many times each feature passed filtering. The top 5 features were selected as those 5 that passed filtering most often.

The performance of the KNN classifiers made with each of the 3 sets of top-ranked features was evaluated using the test set of samples from the OBS arm and the whole set of ACT samples. For approaches (b) and (c) 5 features were used and for approach (a) 6 features were used as there was a tie for the 5$^{th}$ rank. The features (genes) used are listed in table 3.

TABLE 3

Features (genes) selected with approaches (a)-(c)

| (a) Prognostic | (b) Double prognostic | (c) Double predictive |
|---|---|---|
| SFRP1 | NTSR1 | SAMM50 |
| EHD1 | HEY1 | DPAGT1 |
| FAM5B | GAR1 | FAM192A |
| SMC6 | RBM23 | ZMYM6 |
| HERC5 | HHLA2 | LUC7L |
| KERA | | |

We used k=7 for the classifier definition at step 24, but similar results would be expected for other k such as 5 and 9. The classifiers were trained on a subset of samples from the OBS arm (32 of the 62 samples). Of the 32 OBS patients used for training the classifier, the 16 patients with shortest survival times (regardless of censoring) were defined as the "Early" class and the 16 patients with the longest survival times (regardless of censoring) were defined as the "Late" class. The remaining 30 samples in the OBS arm and all the samples from the ACT arm were not used in training and were kept aside as a test set for evaluating classifier performance.

Figure 6C:
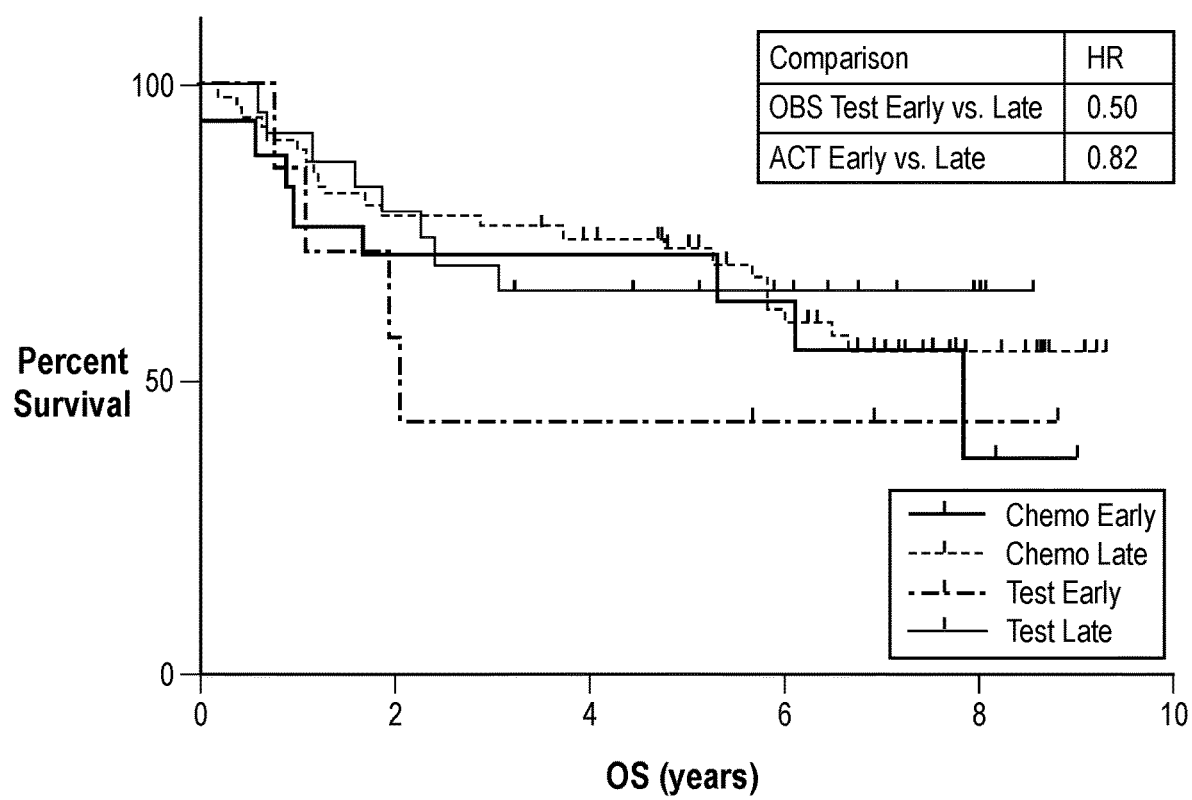

The results are summarized in the FIGS. 6A-6C as Kaplan-Meier plots of percent survival as a function of overall survival, along with Hazard Ratio statistics (HR). In FIG. 6A (simple prognostic filter), the selected features produce a large split between groups within the OBS arm samples not used in training. The groups in the ACT arm split in OS in the opposite direction, with "Early" patients having better outcomes than the "Late" patients. In FIG. 6B (double prognostic filter), the application of similar filters on HR between groups in the ACT arm and the OBS arm selects features which produce similar HRs between groups in both arms when evaluated on the samples not used in training. In FIG. 6C (double predictive filter), the application of the double predictive filter leads to a split in the OBS arm, but close to no separation in the ACT arm (as selected for in the filtering). The "Late" patients gain very little benefit from ACT, whereas the "Early" patients clearly perform better when receiving ACT.

It is clear that changing the filtering used in feature selection tunes the performance of the final classifier in the desired clinical directions—toward a general prognostic classifier with similar behavior across treatment arms or toward a predictive classifier with a split between treatment arms in the "Early" group and not in the "Late" group.

Hence, this example illustrates that a set of features and a test or classifier using them can be tuned easily to fit a particular clinical application and so meet the particular clinical unmet need.

Example 3

Feature Deselection as Input to a Subsequent Classifier Development Exercise

While the Examples 1 and 2 shown here demonstrate the capacity of the method of FIG. 3 for feature selection, the method of FIG. 3 is equally useful for feature deselection. In a robust manner, the method can identify features which only pass filtering in very few realizations. These features only pass filtering for very particular configurations of the training subset, and hence are likely not have any value for classification that can generalize to unseen datasets. The list of features can thus be pared down to deselection or remove such "junky" features can be used. The reduced set of features can then, for example, be used for generating a final classifier in accordance with FIGS. 1-3 or as input to a subsequent classifier generation method, such as for example the CMC/D classifier development process of out co-pending US patent application cited previously.

As a hypothetical example, the genomic data described in Example 2 could be subject to the processing of FIGS. 1-3 and the filtered feature list created in FIG. 3 could be used to deselect some fraction of the 13,000+ genomic features in the data set which do not pass the filtering step and therefore are deemed to not contribute to classification performance, say, 50 or 75 percent of such features. Then, with the reduced set of features, a new final classifier is generated from this reduced feature set. As indicated in FIG. 1, at step 26, the data set with this reduced set of features is supplied to a CMC/D classification development process of our prior U.S. patent application, and the resulting classifier is generated and defined, as described in the genomic example of the prior application, at step 28.

As another example, the procedure of FIG. 3 is performed in order to deselect some of the 300 mass spectral features of Example 1. In particular, the filtered feature list is used to eliminate or deselect 200 "junky features" of the 300 features. The remaining 100 features+APF are then supplied to a CMC/D classifier generation process at step 26 of FIG. 1, and that process, per our prior patent application cited previously is performed and a final CMC/D classifier is defined at step 28. This final classifier is then used for early detection of HCC in high risk populations at step 30.

As another example, the procedure of FIG. 3 is performed in order to deselect some of the 300 mass spectral features of Example 1. In particular, the filtered feature list is used to eliminate or deselect 200 "junky features" of the 300 features. A simple KNN classifier is then defined at step 24 of FIG. 1 using the remaining 100 features+APF.

Further Considerations

Figure 7:
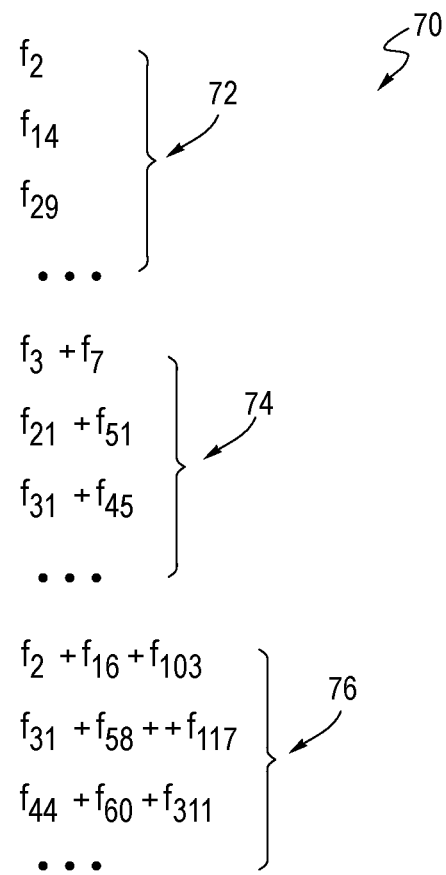
FIG. 7 is an illustration of a filtered feature list created using the process of FIG. 3, step 110, showing the filtered feature list including single features (72), pairs of features (74) and triplets of features (76); the pairs and triplets of features are optionally obtained when performing a multivariate feature selection process.

Examples 1 and 2 have only considered univariate feature selection. However, if one uses a classifier within the feature (de)selection method that can combine features in an inherently multivariate manner, such as the KNN classifier we used here, one can extend this method to select combinations of features that can act as multivariate biomarkers. For example, suppose one is interested in looking for combinations of five features that, together, have multivariate classification power, one could repeat the filtering process over all combinations of five features (generated or defined in step 114 and then used in loop 152 in FIG. 3) rather than over all individual features, and then select the combinations of such five features that pass filtering most often across the subset realizations. Obviously, one could do this multivariate feature selection exercise with some other number of features (s) besides 5, such as 2, 3 or even 10. FIG. 7 shows the filtered feature list 70 with individual features (72), ordered pairs of features (74) and ordered triplets of features (76). As the number of features (parameter s) grows, the number of all possible combinations of features in feature space grows very quickly (combinatorially) and thus considerations of computer processing time and computing power may come into play in performing the feature selection process of FIG. 3, particularly if the absolute number of features in the feature space is large, say 10,000, and s is also large.

It will also be apparent that many of the steps of FIGS. 1-3 will be implemented in a programmed general purpose computer (FIG. 2, 42) equipped with a memory storing the measurement data, pre-processing instructions, and code for implementing the bagged filtering process of FIG. 3. After execution of the process of FIG. 1, the definition of the final classifier of FIG. 1 (step 24 or step 28) will typically be specified in memory of the computer. The resulting computer, with the selected or deselected features as a result of execution of FIGS. 1-3, is an improved machine in that it has an improved ability to perform classification of test samples, as demonstrated in Examples 1 and 2.

From the above discussion, it will be appreciated that we have described a novel and useful method of feature selection and deselection. It is an ensemble-based method and so has the robustness advantages that this bagging approach can provide. It is also easily used across a wide variety of clinical data types. The filters can be designed to deal with discrete classes, continuous variables, and censored time-to-event data. Hence, biomarkers can be identified and tests developed for a wide variety of clinical problems with all types of endpoint or category data. The method is uniquely suited to allow for tuning to the particular clinical question under consideration to produce a test or biomarkers tuned to the particular unmet clinical need. In particular it can avoid known and suspected confounding factors in development data and tune biomarkers and tests to be independent of specific clinical factors.

To summarize, we have disclosed a method improving the functioning of a computer as a classifier by selecting or deselecting one or more features in a data set for generating the classifier. The method includes the steps of:

a) obtaining physical measurement data from a development set of samples (step 12, FIG. 1, e.g., mass spectrometry, genomic or proteomic assay, mRNA expression levels, etc.) and a class label for each of the samples in the development set, the physical measurement data comprising a feature value for a multitude of individual features (e.g., mass spectral peaks); and, in a programmed computer performing steps b)-g):

b) separating the data for the development set of samples into two subsets, one of which is used as a training set (FIG. 3, step 102, FIG. 4);

c) defining a classifier using the training subset and at least one of the features (FIG. 3 step 104);

d) applying the classifier defined in step c) to the training subset (FIG. 3 step 106);

e) applying a filter to the performance of the classifier applied in step d) (FIG. 3, step 108, filter defined at step 120), f) adding the at least one of the features used in step c) to a filtered feature list (70, FIG. 7) if the classifier performance passes the filter step e) (FIG. 3 step 110); and g) repeating steps b), c), d), e) and f) for different realizations of the separation of the development set of samples into two subsets, and for different one or more features in the set of features (loop 150 and 152 in FIG. 3); and h) using the filtered feature list (70) to either select features or deselect features from the multitude of individual features (FIG. 1 step 22) for use in a final classifier generated from the development set of samples (FIG. 1, step 24 or step 28).

As explained in Examples 1 and 2, the filter 120 can take of form of a compound filter of two or more criteria separated by a logical operation. As an example, the filter can take the form of two classifier performance criteria separated by a logical AND operation. At least one of the performance criteria is designed to deal with at least one of discrete classes, continuous variables, and censored time-to-event data. As another alternative, the compound filter could take the form of two classifier performance criteria separated by a logical AND operation and wherein one of the classifier performance criteria is classifier performance on a second set of patient samples (other than the development set), such as a set of samples from healthy patients, a set of samples from patients with liver disease but no cancer, a set of patient samples from a second treatment arm of a clinical trial of a drug, etc.

As another example, the samples are obtained from patients grouped in first and second treatment arm groups, and wherein the filter 120 includes (1) classification performance in the form of a hazard ratio between two classes in the first treatment arm group, (2) classification performance in the form of a hazard ratio between the two classes in the second treatment arm group, and (3) a logical operator.

The filter can also take the form a classifier performance threshold in the form of a hazard ratio between two classification groups, e.g., when the filter is defined as a simple filter for example in Table 1 approach 4.

As explained in Example 1, the samples in the development sample set can take the form of a set of blood-based samples and the measurement process can take the form of mass spectrometry, for example patients with liver disease. As an alternative, as explained in Example 2, the samples can come from human patients (e.g., cancer patients) and the measurement process could take the form of a genomic or proteomic assay. For example, the samples are obtained from patients with cancer, the assay is a genomic assay, and wherein the step h) is a selection of a set of features (genes) from the filtered feature list.

In one example, the physical measurement data at step a) includes a first type of measurement data, e.g., mass spectrometry data, and a second measurement process data different from the first measurement process data, such as a genomic or proteomic assay data, e.g., measurement of AFP as explained in Example 1.

In one example, wherein the separation the data for the development set of samples into two subsets, one of which is used as a training set (step b) is performed in a stratified manner based on a clinical consideration in the patient population from which the development set of samples is obtained.

In step h), using the filtered feature list to either select features or deselect features from the multitude of individual features, one can compute a weight for one or more features which pass the filtering step e). For example, the weight can be based on a diversity measure of the classifier defined in step c).

In another example, the measurement process of step a) comprises mass spectrometry, the features comprise integrated intensity values at m/z ranges in a mass spectrum of the samples, and in step b) the development set is separated into M different realizations of a training subset and a second subset (see FIG. 4), and wherein M is an integer greater than the number N of samples in the sample set. The number of features can be greater than 100 and in step (h) the filtered feature list is used to select a subset of the greater than 100 features for the final classifier. For example, in step (h) fewer than 10 features are selected (see Example 1). As another example, the number of features is greater than 100 and wherein in step (h) the filtered feature list is used to deselect some of the greater than 100 features for use in the final classifier, e.g., as input to a subsequent classifier generation method as explained in Example 3.

As noted in Example 2, the measurement data of step a) is data from an assay of mRNA expression levels for each of the members in the development sample set. In one possible example, the assay is of at least 1000 different genes. In step (h) fewer than 10 genes are selected for use in a final classifier. The samples can be obtained from humans, e.g., from cancer patients.

In yet another aspect, a method of improving the functioning of a computer to generate a classifier has been disclosed. The method includes the steps of:
(a) obtaining a development set of samples (FIG. 1 step 10, FIG. 2, blood-based samples 11);
(b) conducting a physical measurement process on the development set of samples and obtaining measurement values (FIG. 1 step 12, mass spectrometry in FIG. 2);
(c) supplying the measurement values to the computer (FIG. 1 step 14, FIG. 2);
(d) with the computer conducting one or more pre-processing instructions on the measurement values (FIG. 1 step 16);
(e) creating a feature table (50) for the samples in the form of a list of features and a measurement value for each of the features for each of the samples (FIG. 1 step 18);
(f) with the computer, conducting a bagged filtering process on the features of the feature table over many different realizations of a separation of the development set into subsets and over one or more sets of features to either identify a subset of features which have classification power or identify a subset of features which do not have classification power ("junky features") (FIG. 1 step 20, FIG. 3, using filtered feature list 70); and
(g) defining a final classifier (FIG. 1, step 24 or resulting from FIG. 1 step 28) identifying (1) a subset of features as a result of the bagged filtering process (f)(e.g., a subset of the features listed in FIG. 7),
(2) parameters for a classification algorithm (e.g., KNN, value of k, etc.), and
(3) a reference set for use with the classification algorithm comprising i) a set of samples from the development set (e.g., the development sets of Example 1 or 2), ii) their associated values for the set of features resulting from process (f) (feature table for each of the features used for classification) and iii) a class label for each of the samples in the reference set, e.g., assigned by an operator at the time of classifier development.

As explained above, the measurement process can take the form of mass spectrometry, a genomic or proteomic assay, assay of AFP expression level, mRNA assay, etc. In a preferred embodiment the classification algorithm is in the form of a k-nearest neighbor classification algorithm, however other classification algorithms based on supervised learning techniques known in the art, such as margin-based classifiers, decision trees, etc. can be used. The precise nature of the classification algorithm is not particularly important. In one embodiment, as explained in Example 3, the final classifier is obtained from a subsequent classifier development exercise using as an input a selected list of features (or the original list of features minus the junky features) and takes the form of a combination of mini-classifiers with drop-out regularization, as explained in our co-pending application Ser. No. 14/486,442 filed Sep. 15, 2014.

In still another aspect, a testing method has been described which includes the steps of: (a) assaying a sample from a lung cancer patient for the expression level of a set of genes listed in Table 3 (see Example 2), and (b) in a programmed computer comparing the expression levels to a reference set including expression levels of the same set of genes of step (a) from a multitude of other lung cancer patients with a classifier and generating a class label for the sample.

In still another example, a programmed computer (FIG. 2, 42) has been described having a memory storing a the definition of filter (FIG. 3, 120) in the form of at least one criterion for classifier performance, and instructions for a central processing unit of the computer 42 for applying the filter to the performance of a classifier defined in the computer operating on many different realizations (FIG. 4) of a separation of a classifier development set into a training subset and a second subset and one or more measurement features of each member in the training subset (see FIG. 3). The memory further storing a filtered feature list (FIG. 3, 110) listing the measurement features that pass the filter after execution of the instructions.

In one embodiment, as explained in Examples 1 and 2, the filter is in the form of a compound filter having two criteria for classifier performance and a logical operation. As one example (see Example 2), the classifier development set consists of measurement data of samples obtained from patients grouped in first and second treatment arm groups, and wherein the filter includes (1) classification performance in the form of a hazard ratio between two classes in the first treatment arm group, (2) classification performance in the form of a hazard ratio between the two classes in the second treatment arm group, and (3) a logical operator. As explained in Example 1, the filter includes a classification performance criterion on a second set of samples other than the development set of samples, e.g., a set of samples from a healthy population or a set of samples from patients with liver disease but no cancer. As explained in Example 1, the measurement features can take the form of integrated intensity values at m/z ranges in a mass spectrum of each of the development set of samples. The development set is separated into M different realizations of a training subset and a second subset (see FIG. 4), and wherein M is an integer greater than the number N of samples in the development set of samples.

While presently preferred and alternative embodiments have been described with particularity, it will be understood that all questions concerning the scope of the invention will be answered by reference to the appended claims.

We claim:

1. A method improving the functioning of a computer as a classifier by selecting or deselecting one or more features in a data set for generating the classifier, comprising the steps of:
   a) obtaining physical measurement data from a development set of samples and a class label for each of the samples in the development set, the physical measurement data comprising a feature value for a multitude of individual features; and, in a programmed computer performing steps b)-g):
   b) separating the data for the development set of samples into two subsets, one of which is used as a training set;
   c) defining a classifier using the training subset and at least one of the features;
   d) applying the classifier defined in step c) to the training subset;
   e) applying a filter to the performance of the classifier applied in step d),
   f) adding the at least one of the features used in step c) to a filtered feature list if the classifier performance passes the filter step e);
   g) repeating steps b), c), d), e) and f) for different realizations of the separation of the development set of samples into two subsets, and for different one or more features in the set of features; and
   h) using the filtered feature list to either select features or deselect features from the multitude of individual features for use in a final classifier generated from the development set of samples.

2. The method of claim 1, wherein the filter comprises a compound filter of two or more criteria separated by a logical operation.

3. The method of claim 2, wherein the filter comprises two classifier performance criteria separated by a logical AND operation and wherein at least one of the performance criteria is designed to deal with at least one of discrete classes, continuous variables, and censored time-to-event data.

4. The method of claim 1, wherein the samples comprise a set of blood-based samples and the measurement process comprises mass spectrometry.

5. The method of claim 1, wherein the samples comprise a set of samples from human patients and the measurement process comprises a genomic or proteomic assay.

6. The method of claim 5, wherein the samples are obtained from patients with cancer, the assay is a genomic assay, and wherein the step h) is a selection of a set of features (genes) from the filtered feature list.

7. The method of claim 5, wherein the assay is an assay of mRNA expression levels.

8. The method of claim 7, and wherein the assay is of at least 1000 different genes, and wherein the step (h) fewer than 10 genes are selected for use in a final classifier.

9. The method of claim 7, wherein the samples are obtained from cancer patients.

10. The method of claim 1, wherein the samples comprise blood samples obtained from humans with liver disease.

11. The method of claim 1, wherein the filter comprises two classifier performance criteria separated by a logical AND operation and wherein one of the classifier performance criteria is classifier performance on a set of patient samples obtained from patients without cancer.

12. The method of claim 1, wherein the filter comprises two classifier performance criteria separated by a logical AND operation and wherein one of the classifier performance criteria is classification performance on a second set of samples separate from the development set of samples.

13. The method of claim 1, wherein the physical measurement process includes a first measurement process and a second measurement process different from the first measurement process.

14. The method of claim 13, wherein the first measurement process is mass spectrometry and the second measurement process is a genomic or proteomic assay.

15. The method of claim 1, wherein the separation of step b) is performed in a stratified manner based on a clinical consideration in the patient population from which the development set of samples is obtained.

16. The method of claim 1, wherein the filter includes a performance threshold of a hazard ratio between two classification groups.

17. The method of claim 1, wherein the samples are obtained from patients grouped in first and second treatment arm groups, and wherein the filter includes (1) classification performance in the form of a hazard ratio between two classes in the first treatment arm group, (2) classification performance in the form of a hazard ratio between the two classes in the second treatment arm group, and (3) a logical operator.

18. The method of claim 1, wherein the using step (h) comprises computing a weight for one or more features which pass the filtering step e).

19. The method of claim 18, wherein the weight is based on a diversity measure of the classifier defined in step c).

20. The method of claim 1, wherein the measurement method comprises mass spectrometry, the features comprise integrated intensity values at m/z ranges in a mass spectrum of the samples, and wherein the development set is separated into M different realizations of a training subset and a second subset, and wherein M is an integer greater than the number N of samples in the sample set.

21. The method of claim 20, wherein the number of features is greater than 100 and wherein in step (h) of the method of claim 1 the filtered feature list is used to select a subset of the greater than 100 features for the final classifier.

22. The method of claim 21, wherein in step (h) fewer than 10 features are selected.

23. The method of claim 20, wherein the number of features is greater than 100 and wherein in step (h) of the method of claim 1 the filtered feature list is used to deselect some of the greater than 100 features for use in the final classifier.

24. The method of claim 1, wherein in step c) the classifier is defined using two or more of the features in combination and wherein in step g) the process is repeated for each realization of the separation of the development set of samples into two subsets and, for each realization for all possible combinations of the two or more features.

* * * * *